US00PP33950P2

(12) United States Plant Patent
Cousins

(10) Patent No.: US PP33,950 P2
(45) Date of Patent: Feb. 15, 2022

(54) GRAPEVINE PLANT NAMED 'EJG THREE'

(50) Latin Name: ***Vitis interspecific* hybrid**
Varietal Denomination: EJG Three

(71) Applicant: E&J Gallo Winery, Modesto, CA (US)

(72) Inventor: Peter Samuel Melugin Cousins, Modesto, CA (US)

(73) Assignee: E. & J. Gallo Winery, Modesto, CA (US)

( * ) Notice: Subject to any disclaimer, the term of this patent is extended or adjusted under 35 U.S.C. 154(b) by 0 days.

(21) Appl. No.: 17/351,074

(22) Filed: Jun. 17, 2021

(51) Int. Cl.
*A01H 6/88* (2018.01)
*A01H 5/08* (2018.01)

(52) U.S. Cl.
USPC ..... Plt./205

(58) Field of Classification Search
USPC ..... Plt./205
See application file for complete search history.

*Primary Examiner* — Annette H Para
(74) *Attorney, Agent, or Firm* — Goodwin Procter LLP

(57) ABSTRACT

A new and distinct variety of grapevine plant named 'EJG Three' characterized by production of long, loose clusters of black grapes with a distinct fruity flavor. The grapes are suitable for making wine with fruity and floral (e.g., rose petal) flavors and aromas. 'EJG Three' vines are fertile with spur pruning.

9 Drawing Sheets

Latin name of the genus and species of the plant claimed: The plant claimed relates to a new and distinct variety of *Vitis* interspecific hybrid.

Variety denomination: The plant claimed shall be known as 'EJG Three'.

STATEMENT REGARDING FEDERALLY SPONSORED RESEARCH OR DEVELOPMENT

The present invention is not a subject of any federally sponsored research or development.

BACKGROUND OF THE INVENTION

The new and distinct grapevine described and claimed herein originated from a wine grape breeding program. Hand pollination of the flowers of a non-patented seed parent variety with pollen of a non-patented pollen parent variety was performed in May 2013, and the resulting seeds were germinated in a greenhouse. The seedling vines were planted in a vineyard near Ripperdan, Madera County, Calif. in April 2014. The present variety of grapevine was selected as a single plant in 2015 based on the fruit yield, flavor, and composition, and was first asexually propagated by hardwood cuttings at Arroyo Grande, San Luis Obispo County, Calif. in February 2016. The resulting propagules were planted in the vineyard in April 2016 near Ripperdan, Madera County, Calif. as a replicated planting of ten vines. The resulting vines were found to be true to type, showing attributes of the original vine when observed in fruit for at least four seasons. Wine was made from fruit from these ten vines and the wine was evaluated through chemical and sensory testing.

BRIEF SUMMARY OF THE INVENTION

The following description relates to the 'EJG Three' grapevine when grown under normal horticultural practices near Ripperdan, Madera County, Calif. Some of the characteristics of the grapevine may vary depending upon changes in crop load and/or change of location of cultivation.

The 'EJG Three' grapevine is characterized by producing medium-large loose clusters of medium-sized black grapes (alternatively referred to herein as "fruit" or "berries") with a distinct fruity flavor. 'EJG Three' grapes have normal development of seeds. 'EJG Three' flowers are perfect and self-fertile with functional stamens, viable pollen, and a functional pistil. The skin of 'EJG Three' grapes is medium thick. 'EJG Three' grapes ripen for winemaking each year in September or October. 'EJG Three' is fertile with spur pruning. 'EJG Three' grapes are suitable for wine production and the wine is distinguished by positive fruity and floral (e.g., rose petal) flavor and aromas and attractive red or pink color. The positive color, flavor, and aroma of the wine demonstrate the usefulness of 'EJG Three'.

'EJG Three' differs from its seed parent in several important ways. For example, 'EJG Three' has perfect flowers with normal development of erect stamens, which produce viable pollen, and 'EJG Three' is functionally self-fertile, while the seed parent is pistillate flowered with recurved stamens and the seed parent is functionally self-infertile. The grapes of 'EJG Three' are much larger than the grapes of the seed parent. 'EJG Three' differs from its pollen parent by producing black-skinned grapes, while the pollen parent produces grapes that are yellow in color (described as "white" in viticulture and enology). Microsatellite (e.g., simple sequence repeat) markers were used to develop a DNA fingerprint of 'EJG Three', and a comparison of the 'EJG Three' DNA fingerprint to an extensive, non-public database of grapevine variety DNA fingerprints showed that the 'EJG Three' DNA fingerprint was different from all the other DNA fingerprints. This observation is consistent with the origin of 'EJG Three' as a distinct grapevine that arose from a seed resulting from pollination between varieties.

Commercially grown wine grapevine varieties that are most similar to 'EJG Three' are Turan (non-patented), Muscat Hamburg (non-patented), and Muscat of Alexandria (non-patented). 'EJG Three' differs from Turan in several important ways. For example, 'EJG Three' has much larger clusters and grapes than Turan. 'EJG Three' produces black grapes with colorless or whitish flesh (e.g., not colored), while Turan produces black grapes with red berry flesh due to anthocyanin. 'EJG Three' ripens for winemaking in September or October, while Turan ripens for winemaking in July or August. Turan shoots are strongly erect, while 'EJG Three' shoots are semi-erect. Compared to Muscat Hamburg, 'EJG Three' grapes are deeply colored, with medium thick black skin, while Muscat Hamburg grapes are lightly colored, with thin, pale black skin. The clusters of 'EJG Three' are longer than Muscat Hamburg clusters. Compared to Muscat of Alexandria, 'EJG Three' grapes are black-skinned and highly suitable for the production of red or rosé wines, while Muscat of Alexandria grapes are yellow or green in color and suitable chiefly for the production of white wines.

BRIEF DESCRIPTION OF THE DRAWINGS

The accompanying photographs illustrate 'EJG Three' in full color. The colors are as nearly true as is reasonably possible in a color representation of this type. For reference, many of the photographs include the following: a 24-color card sold by CAMERATRAX, a code number (13147074) that was used for testing 'EJG Three', and gridlines in which each square is 1 cm×1 cm. The grapevines and portions thereof shown in the photographs were grown in the vicinity of Ripperdan, Madera County, Calif. The photographs were obtained during the year 2020 when the grapevines were about four (4) years old.

DETAILED BOTANICAL DESCRIPTION

Figure 1:
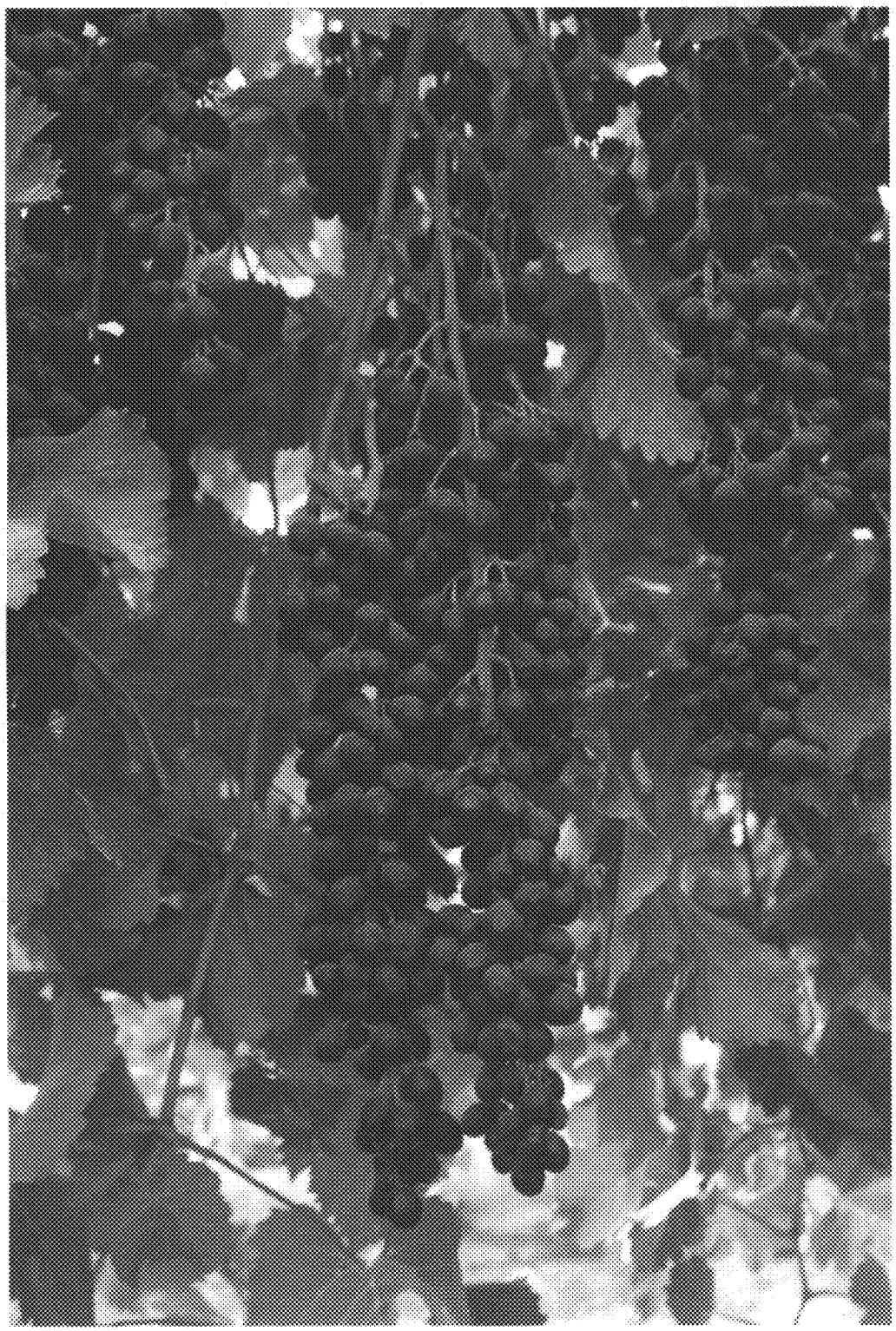
FIG. 1 includes a photograph of a grape cluster on 'EJG Three' during September.
Figure 2:
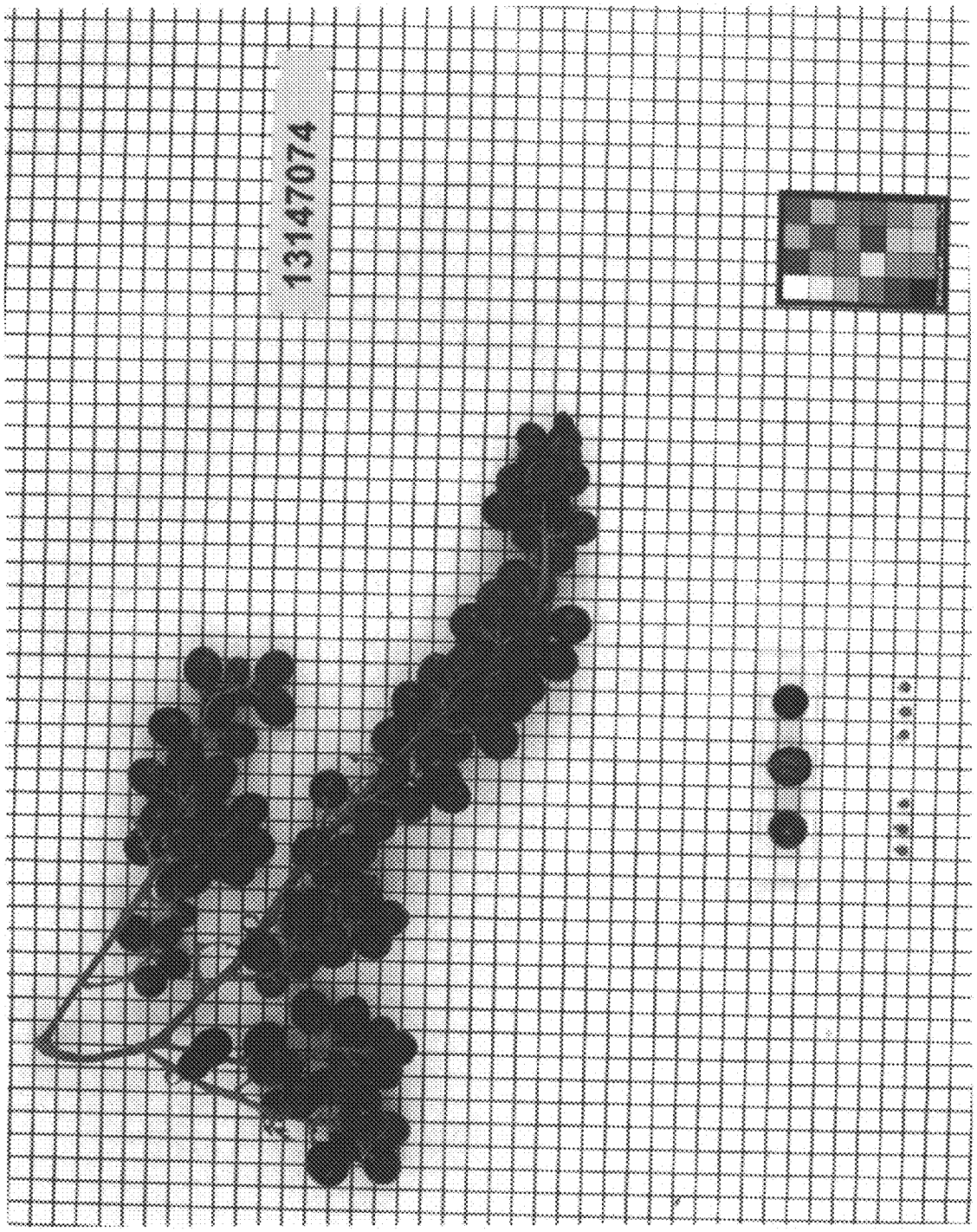
FIG. 2 includes a photograph of a grape cluster, three grapes, and six seeds during September. A grape in the middle of the three grapes has been cut in half.
Figure 3:
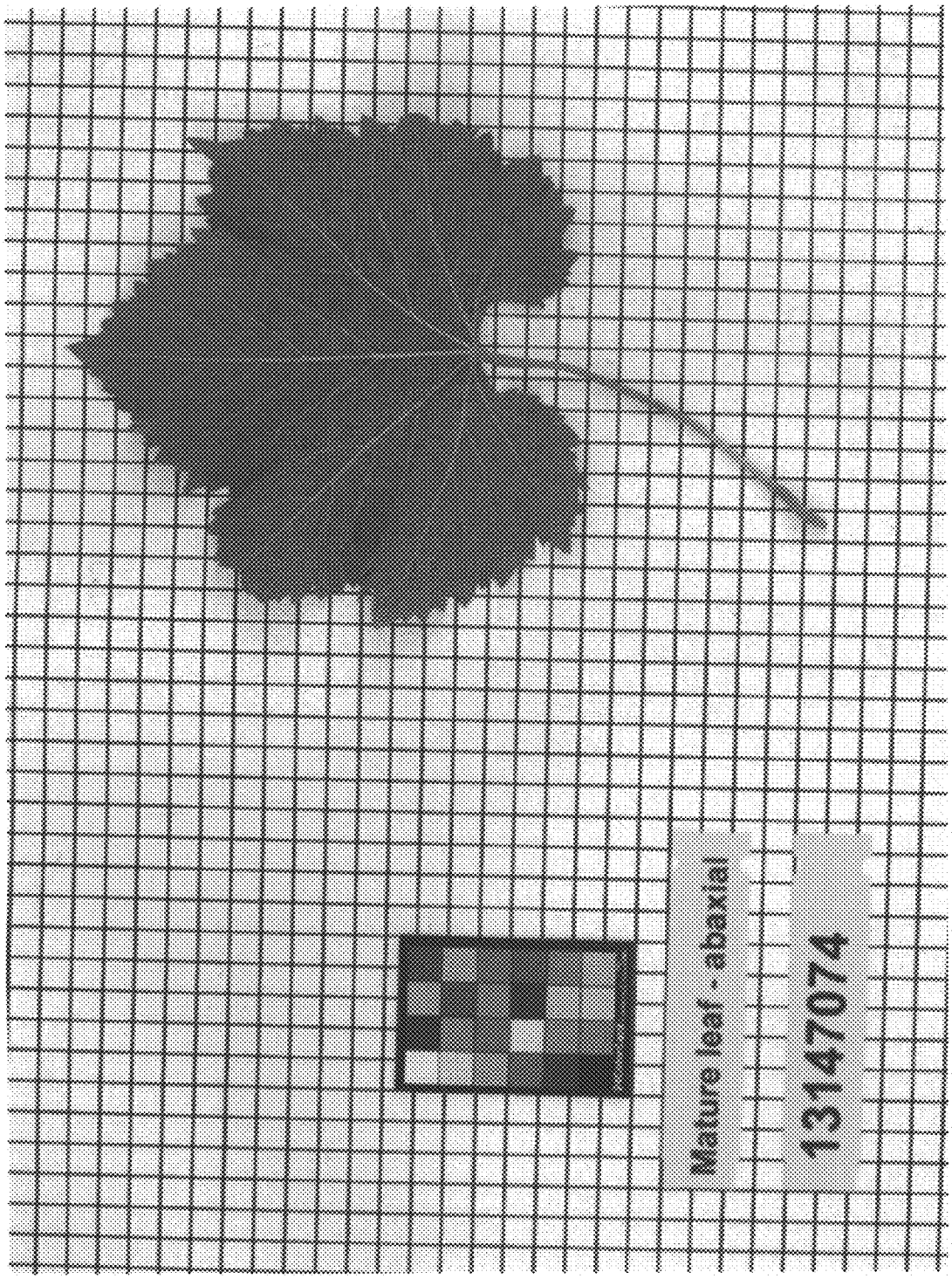
FIG. 3 includes a photograph of an abaxial surface of a mature leaf during July.
Figure 4:
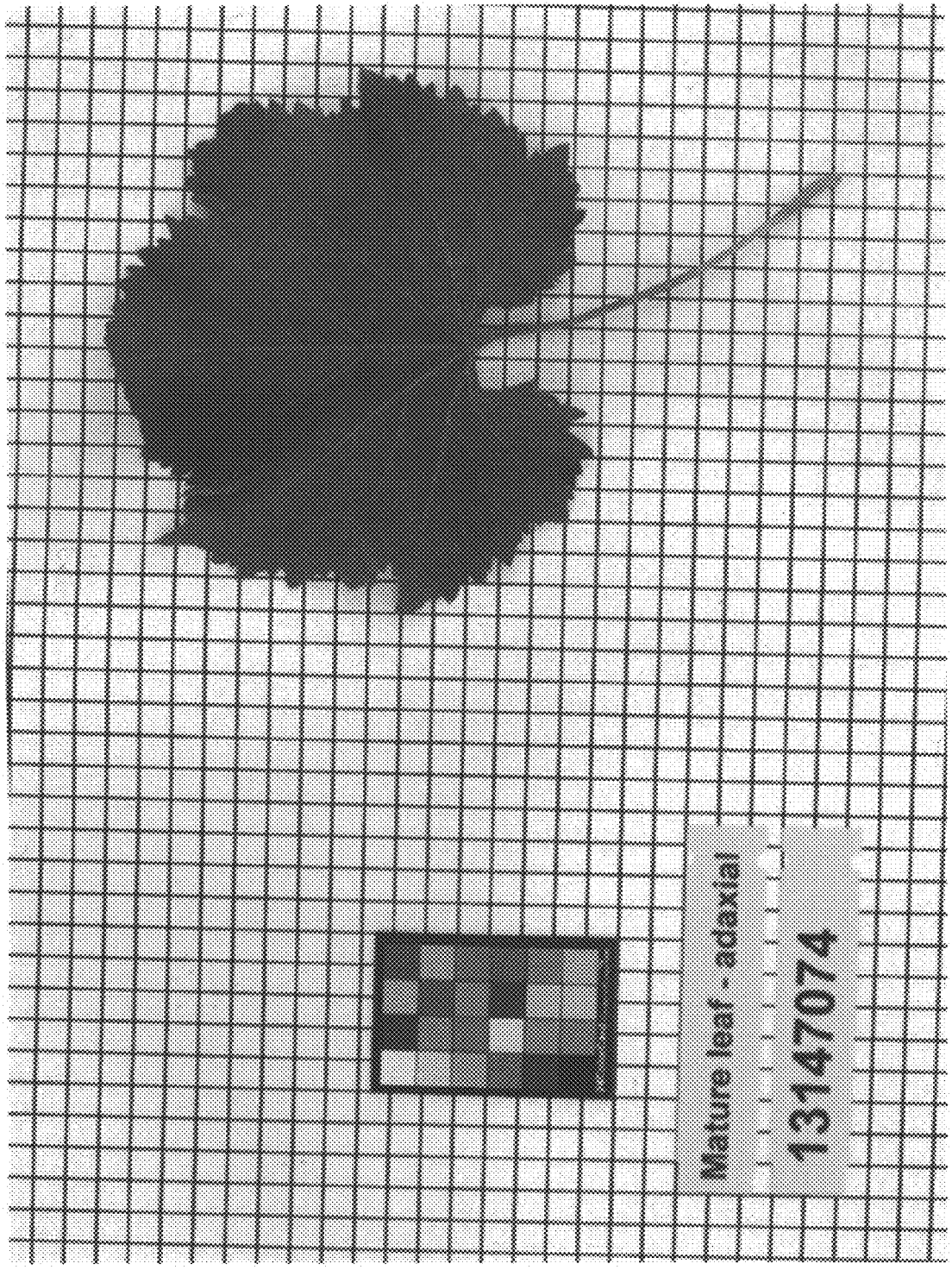
FIG. 4 includes a photograph of an adaxial surface of a mature leaf during July.
Figure 5:
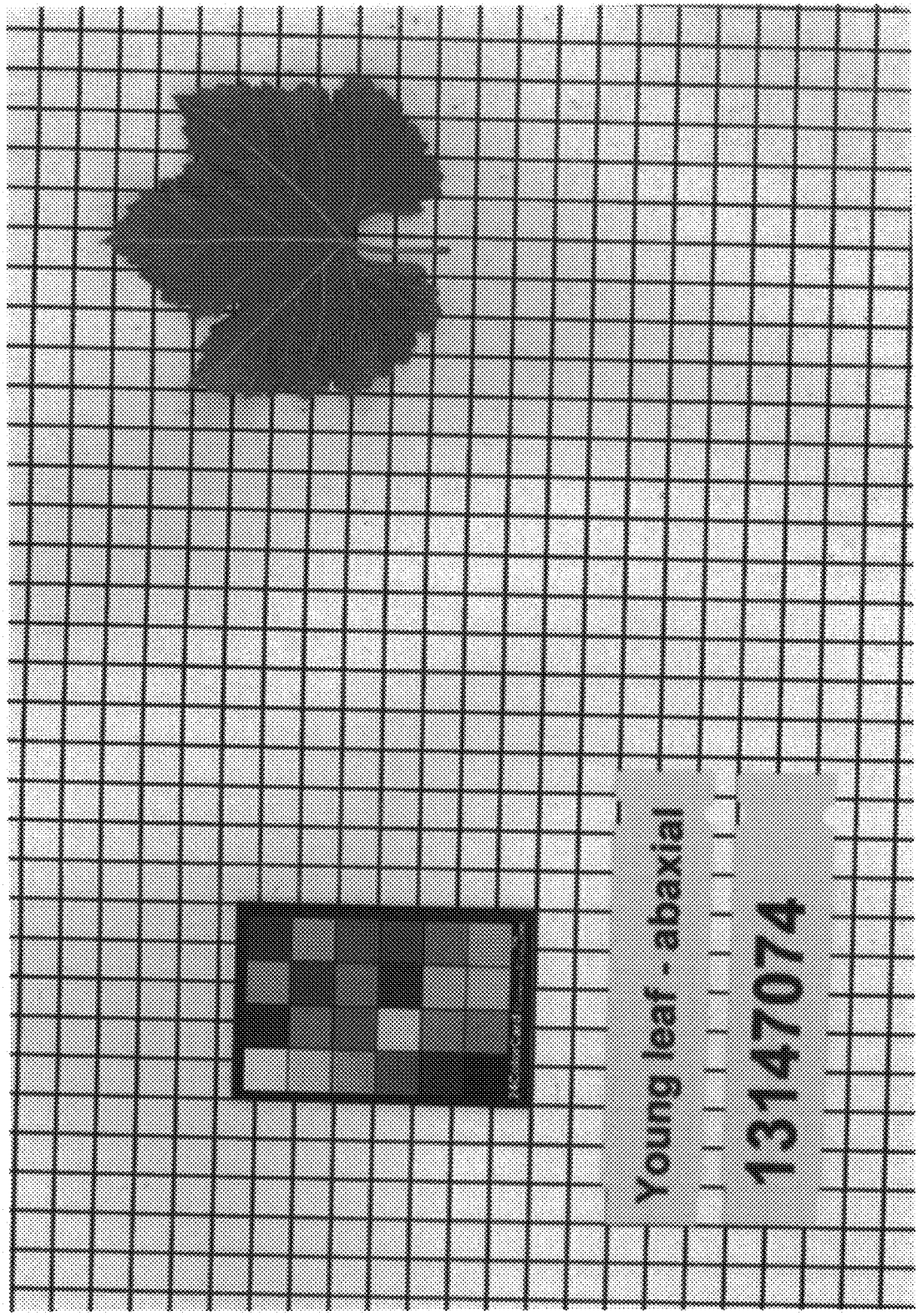
FIG. 5 includes a photograph of an abaxial surface of a young leaf during July.
Figure 6:
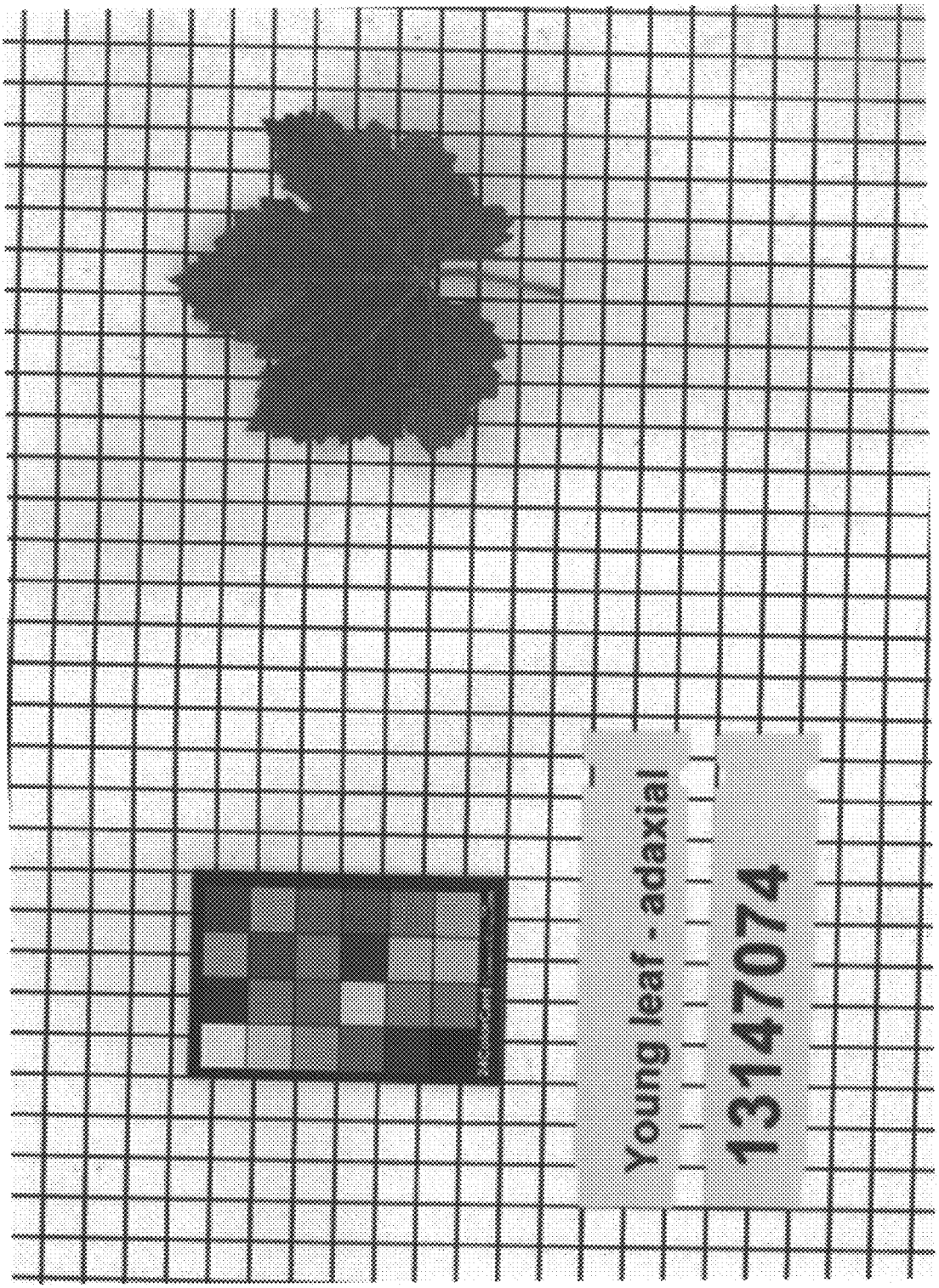
FIG. 6 includes a photograph of an adaxial surface of a young leaf during July.
Figure 7:
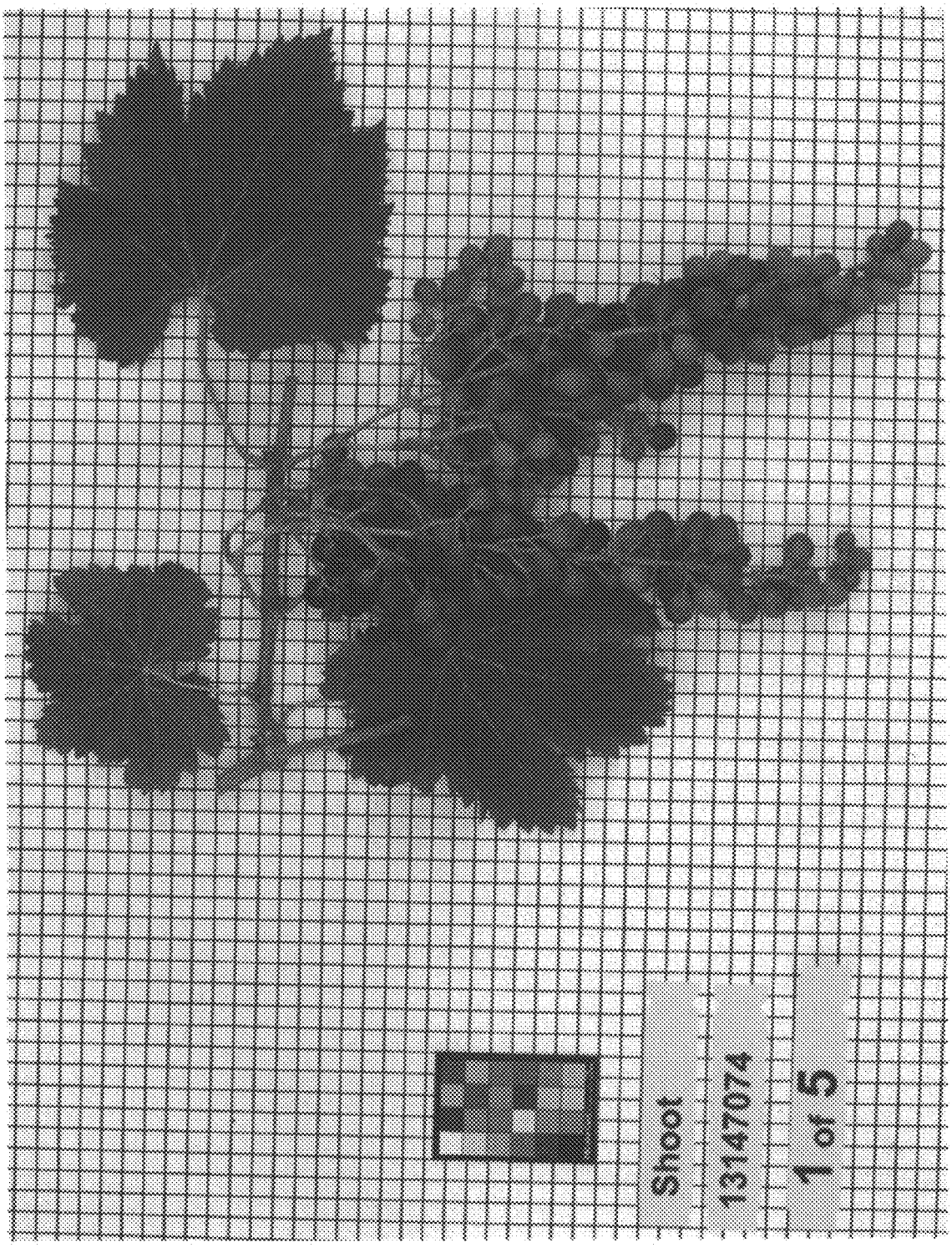
FIG. 7 includes a photograph of a shoot base during July.
Figure 8:
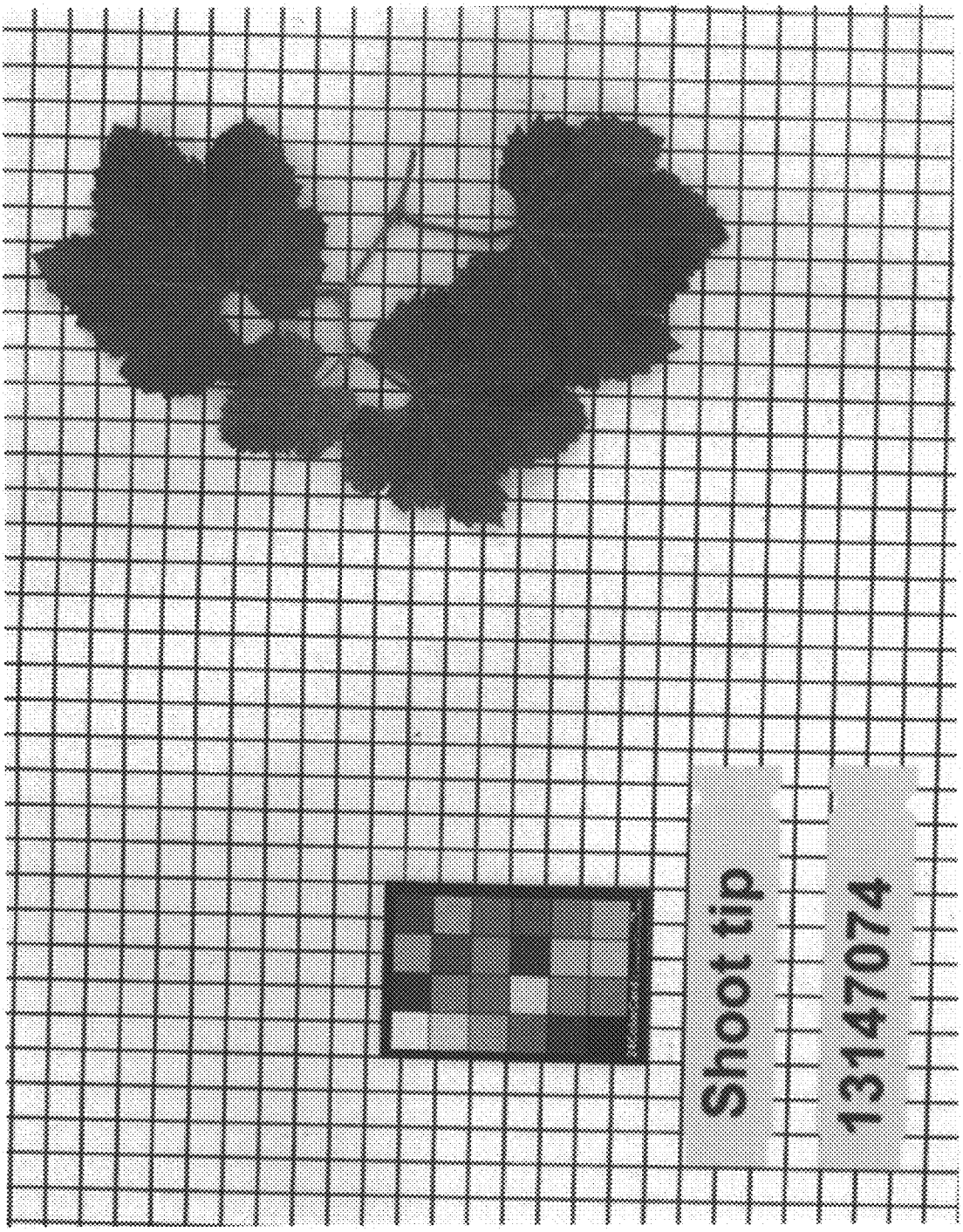
FIG. 8 includes a photograph of a shoot tip during July.
Figure 9:
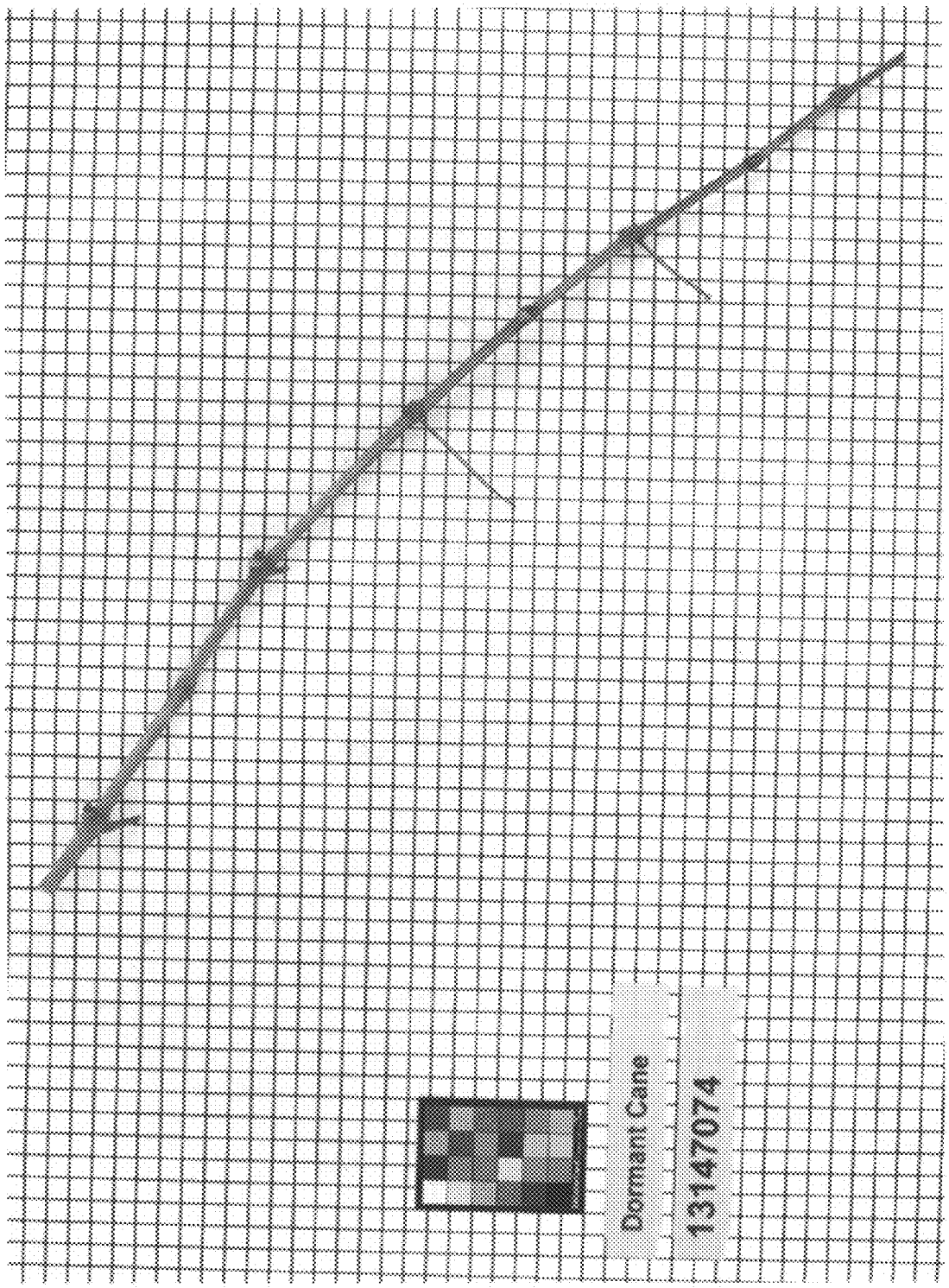
FIG. 9 includes a photograph of a dormant cane during December.

The following detailed description sets forth the distinctive characteristics of 'EJG Three'. Colors refer to the designations of the Munsell Book of Color Glossy Collection, Part No. 40115B, Serial No. 55635311119. The descriptions pertain to grapevines grown in the vicinity of Ripperdan, Madera County, Calif. that were observed during 2020 and other years, and the descriptions are believed to apply to plants of the variety grown under similar conditions elsewhere. The vines from which the observations were made were grown on their own roots (not grafted).

Buds:
- *Bud break date.*—Mar. 9, 2020.
- *Color of dormant buds.*—2.5YR 4/4; Yellow-Red.
- *Length of dormant buds.*—5.1 mm.
- *Width of dormant buds.*—4.2 mm.
- *Number of buds on current, single-season cane.*—20.
- *Shape of dormant buds.*—Pointed.
- *Texture of dormant buds.*—Smooth.

Cluster:
- *Berries per cluster.*—175.
- *Cluster density.*—Loose.
- *Cluster length.*—295.8 mm.
- *Cluster width.*—128.6 mm.
- *Cluster per vine.*—57.
- *Clusters per shoot.*—2.
- *Peduncle length.*—27.4 mm.
- *Weight.*—175 g.

Flower:
- *First bloom date.*—May 5, 2020.
- *Full bloom date.*—May 18, 2020.
- *Flower diameter.*—1.7 mm.
- *Flower length.*—2.8 mm.
- *Flowers per cluster.*—1031.
- *Node location of first inflorescence.*—4.
- *Type.*—Self-fertile hermaphrodite (perfect) with erect stamens.

Fruit:
- *Attachment.*—Easy.
- *Berry flesh color.*—Colorless.
- *Berry skin color.*—5P 2/1; Purple-Red-Purple Grays.
- *Berry diameter at base.*—2.8 mm.
- *Berry diameter at equator.*—16.98 mm.
- *Berry length.*—20 mm.
- *Berry weight.*—1 g.
- *Brush length.*—7.3 mm.
- *Firmness.*—Soft.
- *Flavor.*—Fruity.
- *Harvest date, day of year.*—275.
- *Juiciness.*—Slightly juicy.
- *Pulp texture.*—Slightly meaty.
- *Skin thickness.*—Medium.

Juice:
- *Color.*—Colorless.

Leaves:
- *Arrangement of mature leaves (phyllotaxy).*—Alternate.
- *Autumn coloration of mature leaves, abaxial surface.*—10Y 5/4; Yellow.
- *Autumn coloration of mature leaves, adaxial surface.*—10Y 3/4; Yellow.
- *Color of mature leaves, base abaxial.*—5GY 4/4; Green-Yellow.
- *Color of mature leaves, base adaxial.*—7.5GY 2/4; Green-Yellow.
- *Color of mature leaves, midpoint abaxial.*—5GY 4/4; Green-Yellow.
- *Color of mature leaves, midpoint adaxial.*—7.5GY 2/4; Green-Yellow.
- *Color of mature leaves, terminal abaxial.*—5GY 4/4; Green-Yellow.
- *Color of mature leaves, terminal adaxial.*—7.5GY 2/4; Green-Yellow.
- *Color of veins on mature leaves, abaxial surface.*—2.5GY 8/2; Green-Yellow.

*Color of veins on mature leaves, adaxial surface.*—2.5GY 7/6; Green-Yellow.
*Color of young leaves, base abaxial.*—10Y 5/6; Yellow.
*Color of young leaves, base adaxial.*—10Y 6/10; Yellow.
*Color of young leaves, midpoint abaxial.*—10Y 5/6; Yellow.
*Color of young leaves, midpoint adaxial.*—10Y 6/10; Yellow.
*Color of young leaves, terminal abaxial.*—10Y 5/6; Yellow.
*Color of young leaves, terminal adaxial.*—2.5 GY 5/8 and 5R 2/8; Green-Yellow and Red.
*Length of mature leaves.*—152.1 mm.
*Thickness of mature leaves.*—0.5 mm.
*Width of mature leaves.*—152.2 mm.
*Leaf pubescence on young leaves, abaxial surface.*—Absent.
*Leaf pubescence on young leaves, adaxial surface.*—Absent.
*Margin of mature leaves.*—Serrate with large and small teeth.
*Marginal teeth height.*—5.1 mm.
*Marginal teeth width.*—6.9 mm.
*Number of lobes on mature leaves.*—3.
*Petiole sinus of mature leaves.*—Lobes half open.
*Pubescence on mature leaves, abaxial side.*—Present.
*Pubescence on mature leaves, adaxial side.*—Not present.
*Shape of mature leaves.*—Wedge.
*Surface texture of mature leaves, abaxial side.*—Smooth.
*Surface texture of mature leaves, adaxial side.*—Smooth.
*Vein color of young leaves, abaxial side.*—10Y 8/2; Yellow.
*Vein color of young leaves, adaxial side.*—10Y 8/2; Yellow.
*Venation of mature leaves.*—Regular.

Pedicel:
*Color.*—2.5R 4/6 and 5Y 6/6; Red and Yellow.
*Diameter.*—1.1 mm.
*Length.*—11.2 mm.

Petal:
*Color.*—2.5GY 6/6 and 7.5RP 3/10; Green-Yellow and Red-Purple.
*Number.*—5.

Petioles:
*Color of mature petioles.*—7.5R 2/6; Red.
*Color of young petioles.*—2.5YR 3/6; Yellow-Red.
*Length of mature petioles.*—120.1 mm.
*Thickness at base of mature petioles.*—4.7 mm.
*Pubescence on mature petioles.*—Absent.
*Shape of mature petioles.*—Round.

Pistil:
*Color.*—5GY 5/8; Green-Yellow.
*Length.*—1.6 mm.
*Number.*—1.

Seed:
*Color.*—5R 3/2; Red.
*Length.*—6 mm.
*Number per berry.*—3.
*Seed development.*—Complete.
*Seeds present/absent.*—Present.
*Shape.*—Pyriform.
*Weight.*—0.04 g.
*Width.*—3.8 mm.

Shoots (current-season canes):
*Color of mature, dormant cane.*—7.5YR 4/6; Yellow-Red.
*Color of shoots.*—7.5R 3/4 and 2.5GY 5/6; Red and Green-Yellow.
*Diameter of mature, dormant cane.*—8.9 mm.
*Length of internode above cluster.*—64.7 mm.
*Length of mature, dormant canes.*—90.6 cm.
*Lenticels.*—Absent.
*Node color.*—10Y 6/6; Yellow.
*Shoot attitude.*—Semi erect.
*Texture of mature, dormant canes.*—Smooth.
*Width at node bearing cluster.*—12.9 mm.

Stamen:
*Color of filament.*—2.5GY 9/2; Green-Yellow.
*Number.*—6.

Tendrils:
*Color of mature tendril.*—10R 2/6; Red.
*Length of tendril.*—87 mm.
*Thickness at base of tendril.*—2.2 mm.
*Node location of first tendril.*—8.
*Phyllotaxy (pattern).*—Intermittent.
*Ramification.*—Branched.
*Texture.*—Smooth.

Trunk:
*Color.*—10YR 6/2; Yellow-Red.
*Diameter at 30 cm above soil level.*—184.1 mm.
*Shape.*—Round.

Vine:
*Density of foliage.*—Minimal.
*Growth vigor.*—Moderate.
*Size.*—Moderate.

What is claimed is:

1. A new and distinct variety of grapevine plant named 'EJG Three', substantially as illustrated and described herein.

* * * * *